US010751087B2

(12) United States Patent
Morgan et al.

(10) Patent No.: US 10,751,087 B2
(45) Date of Patent: Aug. 25, 2020

(54) RADIAL BIASING DEVICES FOR TROCAR ASSEMBLY

(71) Applicant: Ethicon LLC, Guaynabo, PR (US)

(72) Inventors: Jerome Morgan, Cincinnati, OH (US); Jason Harris, Mason, OH (US); Andrew Beckman, Cincinnati, OH (US); Robert Koch, Jr., Cincinnati, OH (US); Steven Hall, Cincinnati, OH (US); Kevin Houser, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 315 days.

(21) Appl. No.: 15/720,612

(22) Filed: Sep. 29, 2017

(65) Prior Publication Data

US 2019/0099201 A1 Apr. 4, 2019

(51) Int. Cl.
*A61B 17/34* (2006.01)
*A61B 1/00* (2006.01)

(52) U.S. Cl.
CPC ...... *A61B 17/3462* (2013.01); *A61B 17/3417* (2013.01); *A61B 17/3421* (2013.01); *A61B 1/00154* (2013.01); *A61B 17/3474* (2013.01); *A61B 2017/347* (2013.01); *A61B 2017/3441* (2013.01)

(58) Field of Classification Search
CPC ............ A61B 17/3462; A61B 17/3417; A61B 17/3474; A61B 2017/347; A61B 17/3421; A61B 1/00154; A61B 2017/3441
See application file for complete search history.

(56) References Cited

U.S. PATENT DOCUMENTS

| 2005/0059934 | A1* | 3/2005 | Wenchell | A61B 17/3439 604/167.01 |
| 2008/0287877 | A1* | 11/2008 | Gresham | A61B 17/3421 604/167.06 |
| 2009/0076456 | A1 | 3/2009 | Armstrong et al. | |
| 2010/0036323 | A1* | 2/2010 | Smith | A61B 17/3498 604/167.01 |

(Continued)

FOREIGN PATENT DOCUMENTS

| EP | 1494601 A1 | 1/2005 |
| EP | 1499227 A2 | 1/2005 |

(Continued)

OTHER PUBLICATIONS

ISRWO of corresponding PCT/IB2018/057302 dated Dec. 19, 2018.

*Primary Examiner* — Amber R Stiles
(74) *Attorney, Agent, or Firm* — Vorys, Sater, Seymour and Pease LLP (57) ABSTRACT

A trocar assembly includes a trocar housing that defines a working chamber, and a cannula having a proximal end and a distal end and defining a lumen that extends between the proximal and distal ends. The cannula is coupled to the trocar housing at the proximal end to facilitate communication between the lumen and the working chamber. A radial biasing device is arranged at or near the distal end of the cannula and includes an annular body coupled to the cannula and a compliant stabilizing member transitionable between a relaxed position and an extended position when acted upon by a surgical tool introduced into the lumen and passing through the compliant stabilizing member.

20 Claims, 6 Drawing Sheets

(56) References Cited

U.S. PATENT DOCUMENTS

| | | | |
|---|---|---|---|
| 2010/0100045 A1* | 4/2010 | Pravongviengkham | ................... A61B 17/3421 604/164.09 |
| 2010/0268162 A1* | 10/2010 | Shelton, IV | ....... A61B 17/3421 604/167.01 |
| 2010/0298775 A1* | 11/2010 | Berry | ................ A61B 17/3421 604/167.03 |
| 2011/0046449 A1 | 2/2011 | Minnelli et al. | |
| 2012/0116313 A1 | 5/2012 | Franer et al. | |

FOREIGN PATENT DOCUMENTS

| | | | |
|---|---|---|---|
| WO | 2011082114 | A1 | 7/2011 |
| WO | 20160144170 | A1 | 9/2016 |

\* cited by examiner

RADIAL BIASING DEVICES FOR TROCAR ASSEMBLY

BACKGROUND

During laparoscopic surgery, one or more small incisions are formed in the skin of a patient and a trocar assembly is inserted through the incision to form a pathway that provides access to an internal body cavity, such as the patient's abdomen. The trocar assembly is used to introduce various instruments and tools into the abdomen, as well as to provide insufflation that elevates interior walls of the abdomen.

A trocar assembly generally includes a cannula, an obturator, and a housing. To set the trocar assembly for a surgical operation, the obturator is extended through an inner lumen of the cannula and is used to pierce through the patient's skin to access the abdominal cavity. To penetrate the skin, the distal end of the cannula is placed against an incision in the skin and pressure is applied to the proximal end of the trocar to force the sharp point of the obturator through the skin until it enters the targeted body cavity. The obturator can then be withdrawn, leaving the lumen of the cannula as a path to access the abdominal cavity from outside the body.

The trocar housing is attached to the proximal end of the cannula and defines a working chamber with an open distal end in communication with the lumen of the cannula. Just as the lumen can receive the obturator, it is also sized to receive elongated surgical tools that are axially extended into and withdrawn from the cannula through the proximal end portion of the working chamber.

For surgical operations, a surgeon will normally use a 1:1 pairing of a trocar assembly and a surgical tool. For example, if an 8 mm (diameter) surgical tool will be required for the operation, a corresponding 8 mm (diameter) trocar assembly will be used. In robotic surgery, however, trocar assemblies and surgical tools will not always enjoy a 1:1 pairing. For example, 12 mm (diameter) trocar assemblies are typically used in robotic surgery, which enables use of 12 mm (diameter) surgical tools, such as a surgical stapler.

For some procedures, however, an 8 mm or 5 mm (diameter) surgical tool may be required and will have to pass through the 12 mm trocar assembly. When the trocar assembly and surgical tool pairing is not 1:1, the tip (distal end) of the surgical tool is prone to various types of unintended motion, such as deflection, oscillation in place, and spring back oscillation. Unintended motion of the tip of the instrument can lead to the instrument contacting tissues or damaging them contrary to the intent of the surgeon. These types of motion can each also have an adverse clinical impact. For instance, lacerations or other damage to tissue that is not intended by the surgeon results in potential additional intervention or uncorrectable issues with the tissue.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is related to trocar assemblies and, more particularly, to radial biasing devices used to center surgical tools within a trocar cannula of a trocar assembly and mitigate unwanted oscillation and vibration.

The embodiments described herein provide a radial biasing device that can be incorporated into a trocar assembly at or near the distal end of a trocar cannula. The radial biasing device helps eliminate or significantly minimize unintended oscillation movement and vibration of smaller surgical tools. Moreover, the radial biasing device may also be compliant so that it is able to accommodate larger diameter surgical tools. In one or more embodiments, the radial biasing device is arranged at or near the distal end of the cannula and includes an annular body coupled to the cannula and a compliant stabilizing member transitionable between a relaxed position and an extended position when acted upon by a surgical tool introduced into the inner lumen and passing through the compliant stabilizing member.

Figure 1:
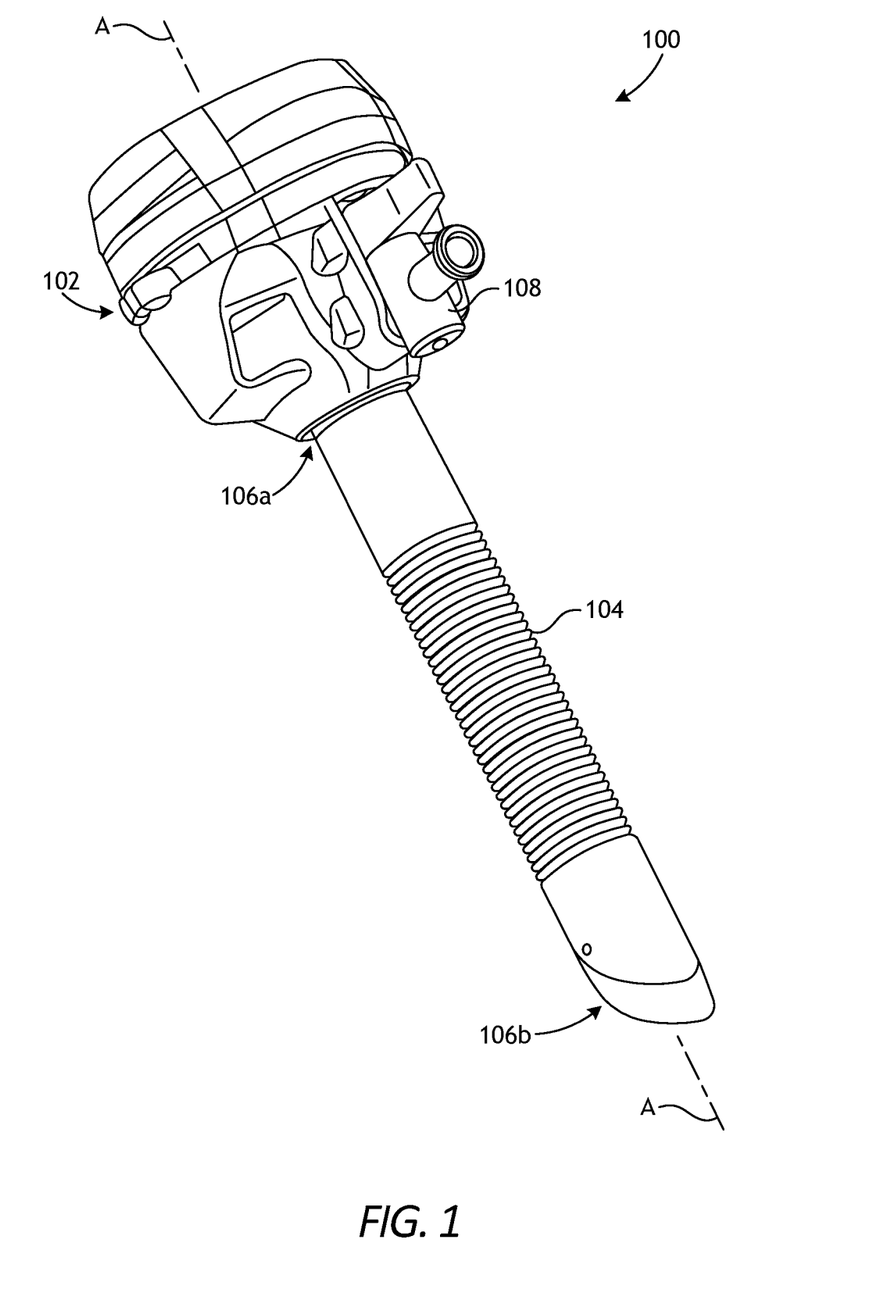
FIG. 1 is an isometric view of an example trocar assembly that may incorporate the principles of the present disclosure.

FIG. 1 is an isometric view of an example trocar assembly 100 that may incorporate the principles of the present disclosure. The depicted trocar assembly 100 is just one example trocar assembly that can suitably incorporate the principles of the present disclosure. Indeed, many alternative designs and configurations of the trocar assembly 100 may employed, without departing from the scope of this disclosure. For example, another suitable trocar assembly that may suitably incorporate the principles of the present disclosure is described in co-owned U.S. Pat. No. 7,918,826 entitled "Trocar Assembly".

As illustrated, the trocar assembly 100 includes a trocar housing 102 and a cannula 104 that has a proximal end 106a and a distal end 106b. The cannula 104 is coupled to the trocar housing 102 at the proximal end 106a and extends distally therefrom. In some embodiments, the cannula 104 may comprise an integral extension of the trocar housing 102. In other embodiments, however, the trocar housing 102 and the cannula 104 may comprise two separate components that can be mated to one another.

The trocar assembly 100 may also include an insufflation valve 108 (e.g., a stopcock valve) coupled to the trocar housing 102 or forming an integral part thereof. The insufflation valve 108 is operable to introduce an insufflation fluid (e.g. carbon dioxide) into the trocar housing 102 and the cannula 104 and subsequently into an inner cavity (e.g., the abdomen) of a patient to elevate the interior walls of the inner cavity. While not shown, the trocar assembly 100 may also include an obturator extendable through the trocar assembly along a centerline A of the trocar assembly 100. When used, the obturator extends through the cannula 104 and out the distal end 106b to penetrate a patient's skin and thereby facilitate access to the abdominal cavity.

Figure 2:
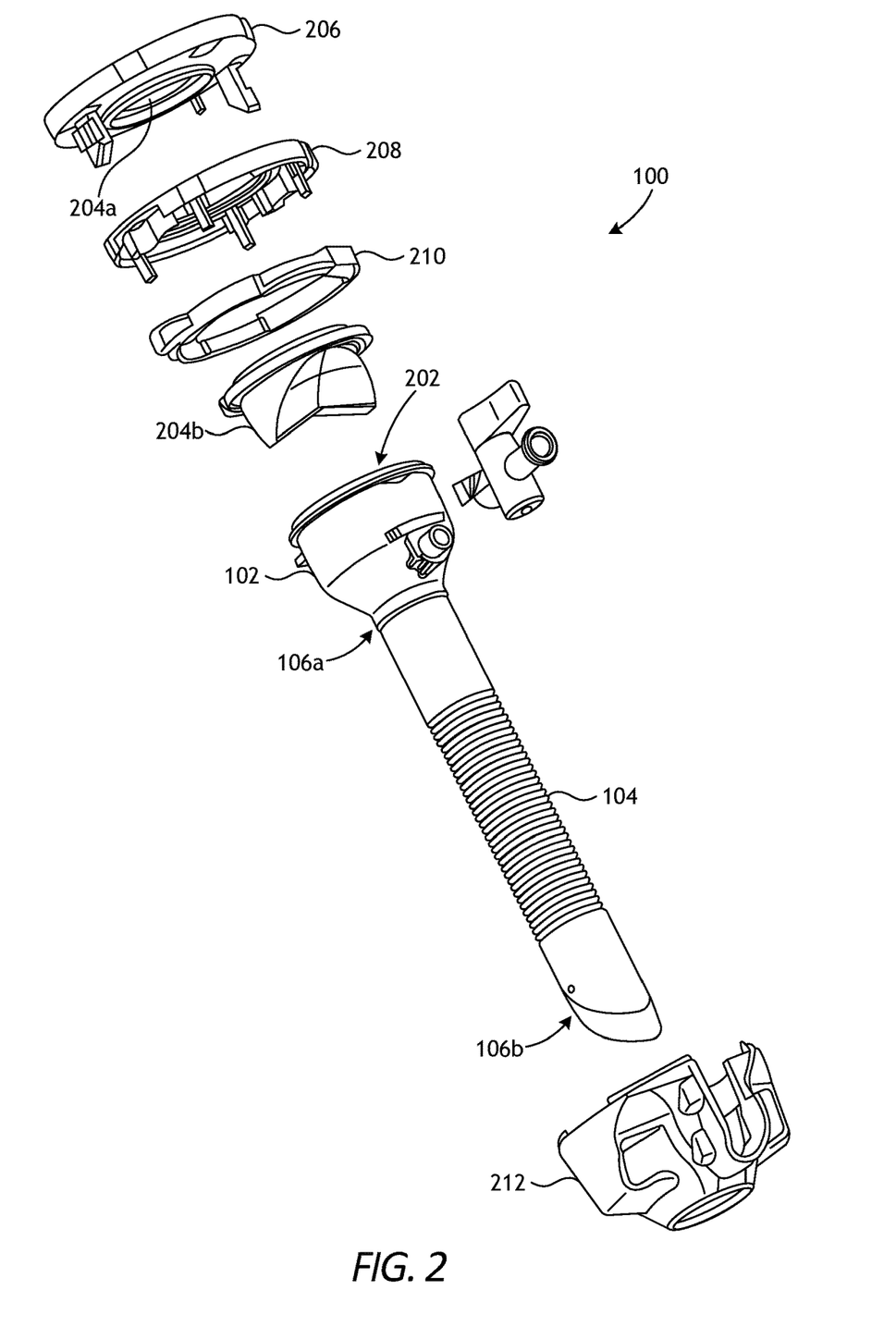
FIG. 2 is an exploded view of the trocar assembly of FIG. 1.

FIG. 2 is an exploded view of the trocar assembly 100 of FIG. 1. The trocar housing 102 provides and otherwise defines a working chamber 202 that communicates with an inner lumen defined within the cannula 104. The lumen is open-ended and extends between the proximal and distal ends 106a, b of the cannula 104.

The working chamber 202 is also open-ended and configured to at least partially receive a first or "proximal" seal assembly 204a and a second or "distal" seal assembly 204b. The first and second seal assemblies 204a, b allow selective sealing of the working chamber 202 during operation. In at least one embodiment, as illustrated, the second seal assembly 204b may comprise a duckbill seal. While two seal assemblies 204a, b are depicted in FIG. 2, the trocar assembly 100 may alternatively include more or less than two seal assemblies, without departing from the scope of the disclosure.

The first and second seal assemblies 204a, b may be secured (at least partially) within the working chamber 202 via a variety of ways. In the illustrated embodiment, for example, a crown ring 206 and a gasket ring 208 may be snap-fit together, and a gasket retainer ring 210 may be configured to secure an attachment between the gasket ring 208 and the trocar housing 102. A housing retainer 212 may then be extended about the exterior of the trocar housing 102 to secure the internal components to the trocar housing 102.

Figure 3:
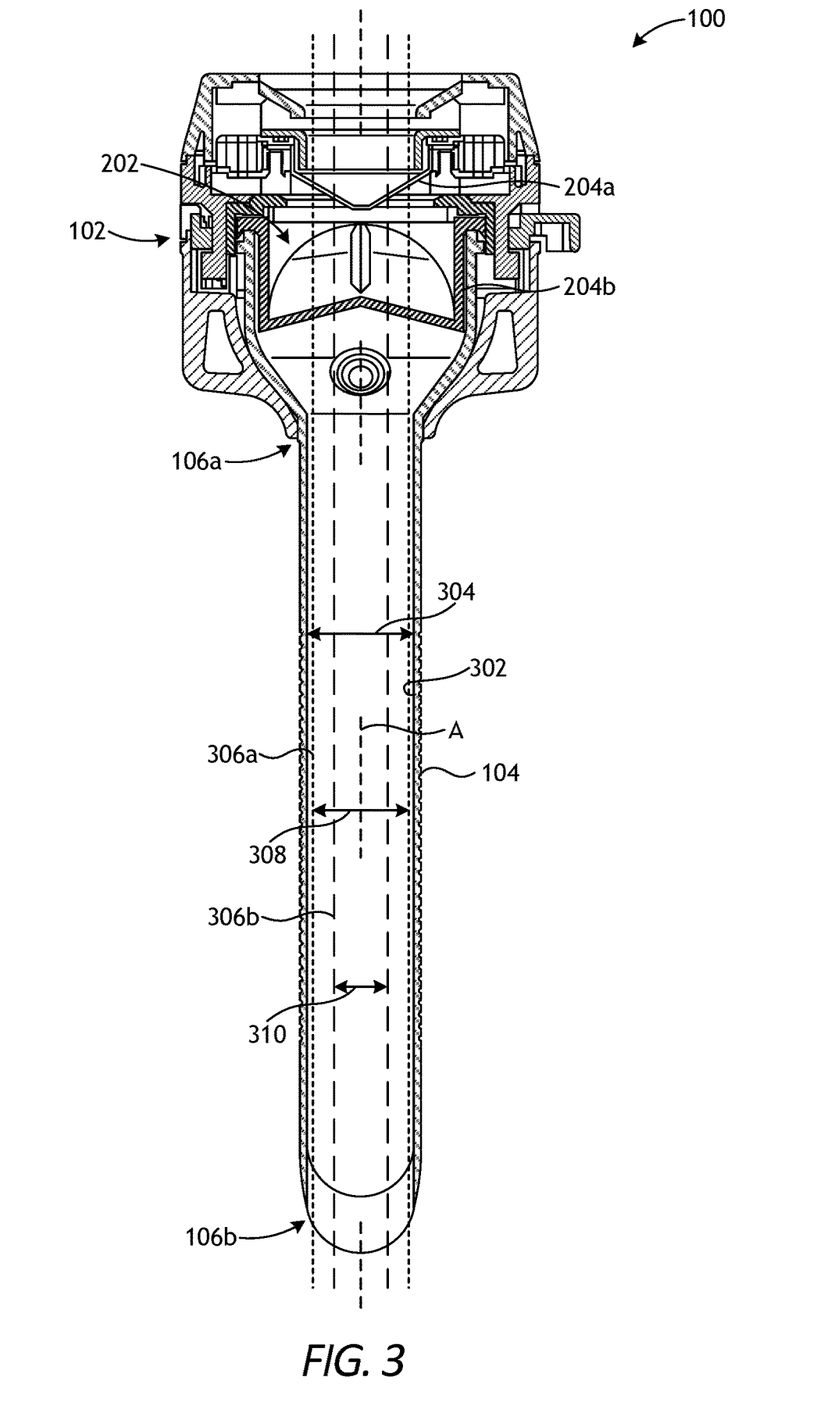
FIG. 3 is a cross-sectional side view of the trocar assembly of FIG. 1.

FIG. 3 is a cross-sectional side view of the trocar assembly 100. As illustrated, the cannula 104 defines and otherwise provides an inner lumen 302 that extends between the proximal and distal ends 106a, b and communicates with the working chamber 202 provided by the trocar housing 102. The lumen 302 exhibits an inner diameter 304 configured to receive surgical tools having an outer diameter equal to (i.e., slightly less than equal) or less than the inner diameter 304.

In at least one embodiment, the inner diameter 304 may be sized to receive a 12 mm surgical tool. In such embodiments, the trocar assembly 100 may be referred to and otherwise characterized as a "12 mm trocar," which is commonly used in robotic surgery to accommodate various 12 mm surgical tools, such as surgical staplers. In the illustrated embodiment, a first surgical tool 306a is depicted in dashed lines as extended through the trocar assembly 100 and projecting out each end. While not explicitly shown, as the first surgical tool 306a is extended into the trocar assembly 100, the first and second seal assemblies 204a, b are configured to deform and provide a sealed interface against the outer surface of the first surgical tool 306a.

The first surgical tool 306a exhibits an outer diameter 308 of approximately 12 mm, which is slightly smaller than the inner diameter 304 of the lumen 302. Accordingly, the first surgical tool 306a may be referred to as a "12 mm surgical tool" and the lumen 302 is sized to receive the first surgical tool 306a such that very little space (e.g., less than 1 mm) remains between the inner and outer diameters 304, 308. Consequently, the first surgical tool 306a is generally centered within the cannula 302 along the centerline A at all times, which tends to mitigate unwanted occurrences of deflection, oscillation, and vibration of the first surgical tool 306a.

At times, however, smaller surgical tools may need to be introduced into the trocar assembly 100 to perform additional procedures. In the illustrated embodiment, for example, a second surgical tool 306b is depicted in dashed lines as extended through the trocar assembly 100 and projecting out each end. Similar to the first surgical tool 306a, and while not explicitly shown, as the second surgical tool 306b is extended into the trocar assembly 100, the first and second seal assemblies 204a, b are configured to deform and provide a sealed interface against the outer surface of the second surgical tool 306b.

The second surgical tool 306b exhibits an outer diameter 310 that is smaller than the outer diameter 308 of the first surgical tool 306a, and smaller than the inner diameter 304 of the lumen 302. In some applications, for example, the outer diameter 310 may be approximately 8 mm. In such applications, the second surgical tool 306b may be referred to as an "8 mm surgical tool." Alternatively, the outer diameter 310 may be approximately 5 mm, and the second surgical tool 306b may instead be referred to as a "5 mm surgical tool."

Since the outer diameter 310 of the second surgical tool 306b is much smaller than the inner diameter 304 of the lumen 302, the second surgical tool 306b will rarely (if ever) be centered within the cannula 302 along the centerline A during operation. Rather, during operation the second surgical tool 306b will continuously be prone to deflection, oscillation in place, spring back oscillation, and vibration as the second surgical tool 306b is manipulated in various directions. Such unintended motion of the second surgical tool 306b can lead to the instrument contacting tissues or damaging them contrary to the intent of the surgeon. These types of motion can also each have an adverse clinical impact as lacerations or other damage to tissue that is not intended by the surgeon can require additional intervention or uncorrectable issues with the tissue.

According to embodiments of the present disclosure, a radial biasing device may be incorporated into the trocar assembly 100 at or near the distal end 106b of the cannula 104 to eliminate or significantly minimize unintended oscillation movement and vibration of smaller surgical tools, e.g., the second surgical tool 306b. The radial biasing device may also be compliant so that it does not unduly obstruct the first surgical tool 306a but is instead able to accommodate the larger-diameter features of the first surgical tool 306a.

Figure 4A:
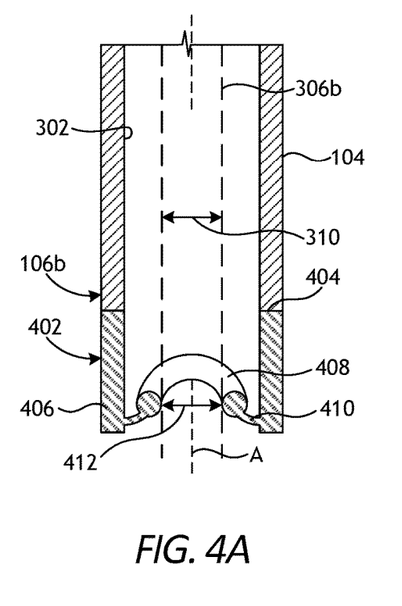
FIGS. 4A and 4B are cross-sectional side views of an example radial biasing device.
Figure 4B:
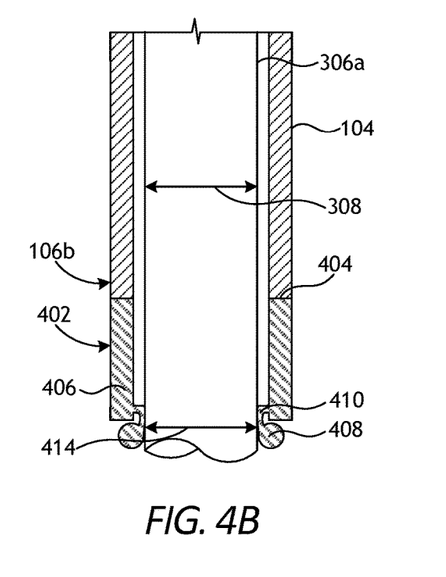

FIGS. 4A and 4B are enlarged cross-sectional side views of an example radial biasing device 402 that may be used with the trocar assembly 100 of FIGS. 1-3, according to one or more embodiments of the present disclosure. The radial biasing device 402 may be coupled to or otherwise arranged at or near the distal end 106b of the cannula 104. In the illustrated embodiment, the radial biasing device 402 is coupled or attached to the distal end 106b of the cannula 104 at an interface 404 between the annular body 406 and the cannula 104. The radial biasing device 402 may be coupled to the cannula 104 at the interface 404 via a variety of attachment means including, but not limited to, one or more mechanical fasteners, a threaded engagement, welding, ultrasonic welding, overmolding, brazing, an adhesive, an interference fit, a shrink fit, a mechanical attachment (e.g., a bayonet connection), or any combination thereof.

As illustrated, the radial biasing device 402 may include an annular body 406 and a compliant stabilizing member 408 arranged within the annular body 406. In the illustrated embodiment, the compliant stabilizing member 408 is in the form of a ring and is coupled to the annular body 406 with an annular flange 410. The annular body 406 is coupled to the cannula 104 at the interface 404.

In some embodiments, the annular body 406, the compliant stabilizing member 408, and the annular flange 410 comprise a unitary structure that is integrally formed. In other embodiments, however, the compliant stabilizing member 408 and the annular flange 410 may be separable from the annular body 406 and otherwise attachable to the inner radial surface of the annular body 406, without departing from the scope of the disclosure.

All or a portion of the radial biasing device 402 may be made of a pliable or elastic material to enable the radial biasing device 402 to transition (move) between a relaxed position, as shown in FIG. 4A, and an extended position, as shown in FIG. 4B. In some embodiments, however, only the compliant stabilizing member 408 and the annular flange 410 may be made of the elastic material while the annular body 406 may be made of any rigid or semi-rigid biocompatible material, such as a metal or a plastic. Suitable elastic materials include, but are not limited to, rubber (e.g., natural rubber, synthetic rubber, nitrile rubber, silicone rubber, a urethane rubber, a polyether rubber, chloroprene rubber, ethylene propylene diene monomer, styrene-butadiene rubber, etc.), silicone, ethylene vinyl acetate, nylon, vinyl, spandex, polyurethane, polyethylene, polypropylene, or any combination thereof.

Example operation of the radial biasing device 402 is now provided. In FIG. 4A, the radial biasing device 402 is in the relaxed position and the second surgical tool 306b is depicted in dashed lines as extended through the cannula 104 and out the distal end 106b. The second surgical tool 306b also extends through the radial biasing device 402 and, more particularly, through the compliant stabilizing member 408, which exhibits a relaxed inner diameter 412 that is slightly larger than the outer diameter 310 of the second surgical tool 306b. The compliant stabilizing member 408 operates to center the second surgical tool 306b within the lumen 302 and thereby eliminate or significantly minimize unintended oscillation movement and/or vibration of the second surgical tool 306b.

FIG. 4B shows the radial biasing device 402 in the extended position. The radial biasing device 402 is able to transition to the extended position when a surgical tool having an outer diameter larger than the relaxed inner diameter 412 (FIG. 4A) of the compliant stabilizing member 408 is introduced into the cannula 104 and interacts with the radial biasing device 402. In the illustrated embodiment, the first surgical tool 306a is extended through the cannula 104 and forces the compliant stabilizing member 408 out of the annular body 406. More specifically, because the outer diameter 308 of the first surgical tool 306a is greater than the relaxed inner diameter 412 of the compliant stabilizing member 408, the smaller-diameter compliant stabilizing member 408 is forced out of the annular body 406 and otherwise rolled to the exterior as the first surgical tool 306a passes through the radial biasing device 402.

Since the compliant stabilizing member 408 is made of an elastic material, the compliant stabilizing member 408 may be able to radially expand to an extended diameter 414 to accommodate the larger-diameter first surgical tool 306a. Accordingly, the compliant stabilizing member 408 may be configured to compliantly expand and the extended diameter 414 will conform to the outer diameter of the surgical tool passing therethrough. In the illustrated embodiment, the extended diameter 414 is approximately the same size as the outer diameter 308 of the first surgical tool 306a.

In one or more embodiments, the compliant stabilizing member 408 may be lubricious (e.g., slippery or slick), thereby reducing the drag force of any surgical tool passing therethrough. In some embodiments, for example, the elastic material of the compliant stabilizing member 408 may be a lubricious material, such as silicone. In other embodiments, however, the compliant stabilizing member 408 may be coated with a biocompatible lubricious substance or material such as, but not limited to, oil, graphite, TEFLON™, silicone, parylene, medical fluid and any combination thereof.

Figure 5A:
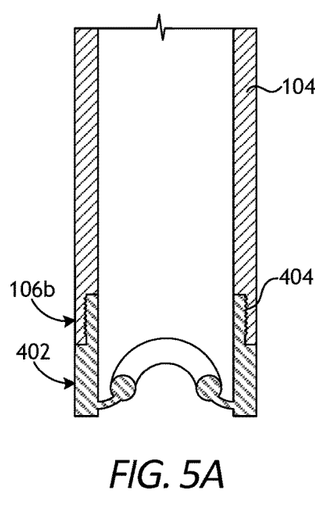
FIGS. 5A-5C depict various ways of attaching the radial biasing device of FIGS. 4A-4B to the distal end of a trocar cannula.
Figure 5B:
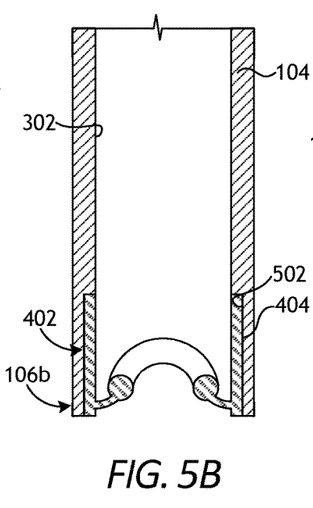
Figure 5C:
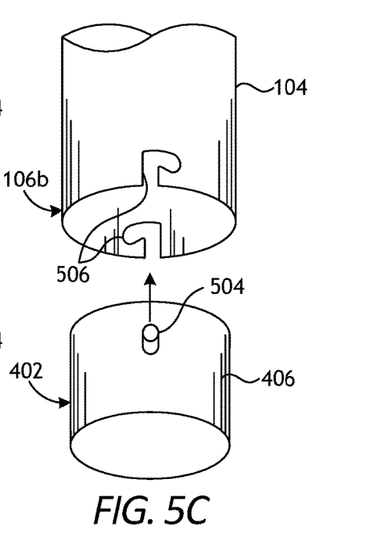

FIGS. 5A-5C depict exemplary ways of attaching the radial biasing device 402 of FIGS. 4A-4B to the distal end 106b of the cannula 104, according to various additional embodiments. In FIG. 5A, the interface 404 between the radial biasing device 402 and the cannula 104 comprises a threaded engagement. Accordingly, in at least one embodiment, the radial biasing device 402 may be threaded to the distal end 106b of the cannula 104.

In FIG. 5B, an annular cavity 502 is defined at the distal end 106b of the cannula 104 and may be sized to receive and seat the radial biasing device 402. Accordingly, in such embodiments, the radial biasing device 402 may be arranged entirely or partially within the lumen 302 of the cannula 104. In such embodiments, the interface 404 between the radial biasing device 402 and the cannula 104 may be provided by a variety of attachment means including, but not limited to, an interference fit (e.g., a press fit), a shrink fit, an adhesive, one or more mechanical fasteners, welding, ultrasonic welding, overmolding, brazing, and any combination thereof.

In FIG. 5C, the radial biasing device 402 may be coupled to the distal end 106b of the cannula 104 via mechanical attachment, shown in FIG. 5C as a bayonet connection. Bayonet connections typically include a cylindrical male connector and a female receptor. In the illustrated embodiment, the annular body 406 provides the cylindrical male connector and the distal end 106b of the cannula 104 provides the female receptor. One or more radial pins 504 (one shown) extend from the outer radial surface of the annular body 406, and one or more matching L-shaped slots 506 (two shown) are defined in the distal end 106b of the cannula 104. To couple the radial biasing device 402 to the distal end 106b, the radial pin(s) 504 slides into the vertical arm of the L-shaped slots 506 and the annular body 406 is then rotated to move the radial pin(s) 504 into the horizontal arm of the L-shaped slots 506.

Figure 6A:
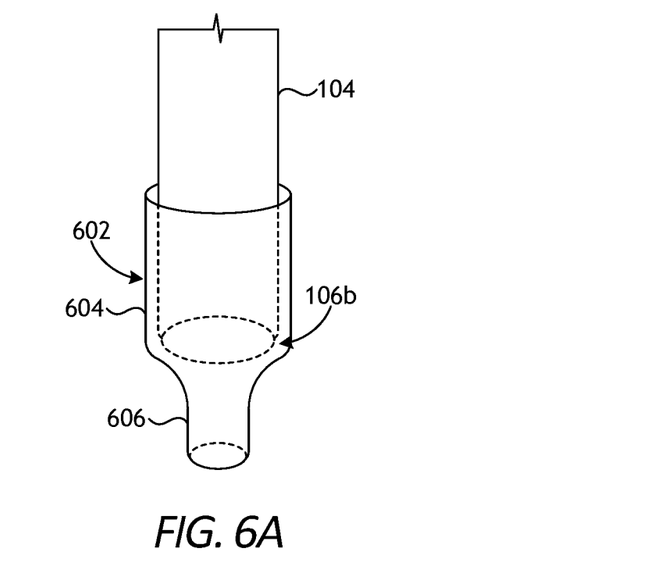
FIG. 6A is a side view of another example radial biasing device that may be used with the trocar assembly of FIGS. 1-3.

FIG. 6A is a side view of another example radial biasing device 602 that may be used with the trocar assembly 100 of FIGS. 1-3, according to one or more embodiments of the present disclosure. Similar to the radial biasing device 402 of FIGS. 4A-4B, the radial biasing device 602 may be coupled to or otherwise arranged at or near the distal end 106b of the cannula 104. Unlike the radial biasing device 402 of FIGS. 4A-4B, however, the radial biasing device 602 may be coupled or attached to the exterior of the cannula 104 at or near the distal end 106b.

As illustrated, the radial biasing device 602 may comprise a covering or "sock" disposed about the distal end 106b of the cannula 104. The radial biasing device 602 may be coupled to the distal end 106b of the cannula 104 via a variety of attachment means including, but not limited to, one or more mechanical fasteners, a threaded engagement, welding, ultrasonic welding, overmolding, brazing, an adhesive, an interference fit, a shrink fit, a mechanical attachment, or any combination thereof.

As illustrated, the radial biasing device 602 may include an annular body 604 and a compliant stabilizing member 606 extending distally from the annular body 604. In the illustrated embodiment, the compliant stabilizing member 606 tapers inward as it extends distally from the annular body 604. In some embodiments, the annular body 604 and the compliant stabilizing member 606 are integrally formed. In such embodiments, the entire radial biasing device 602 may be formed or molded as a unitary structure. In other embodiments, however, the annular body 604 and the compliant stabilizing member 606 may be separate component parts that can be coupled or mated together, without departing from the scope of the disclosure.

Figure 6B:
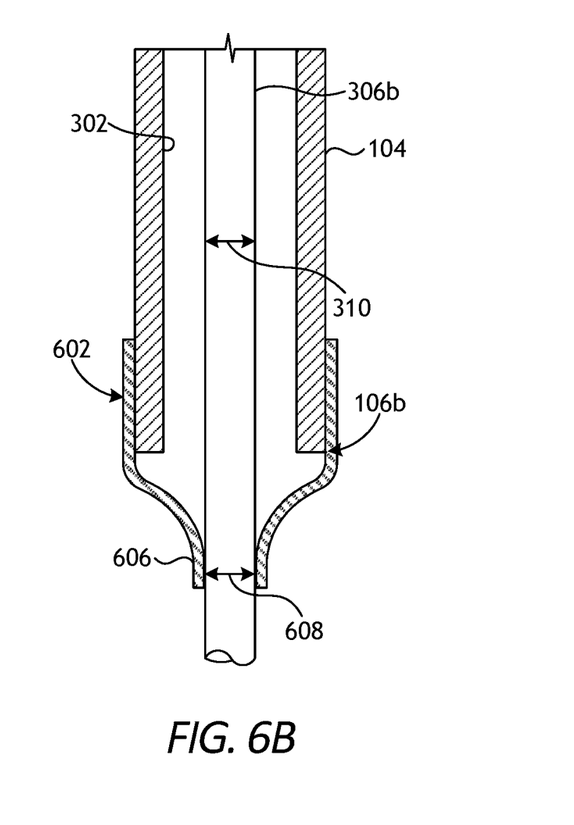
FIGS. 6B and 6C are cross-sectional side views of the radial biasing device of FIG. 6A depicting example operation.
Figure 6C:
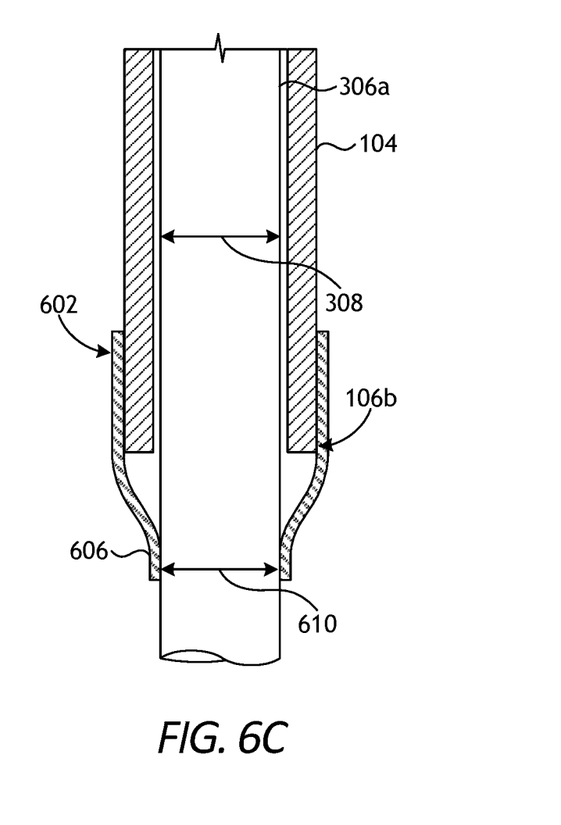

FIGS. 6B and 6C are cross-sectional side views depicting example operation of the radial biasing device 602, according to one or more embodiments. All or a portion of the radial biasing device 602 may be made of a pliable or elastic material to enable the radial biasing device 602 to transition between a relaxed position, as shown in FIG. 6B, and an extended position, as shown in FIG. 6C. Suitable elastic materials include those mentioned herein with respect to the radial biasing device 402 of FIGS. 4A-4B. In some embodiments, however, only the compliant stabilizing member 606 is made of the elastic material while the annular body 604 may be made of a rigid or semi-rigid material, such as a metal or a plastic.

In FIG. 6B, the radial biasing device 602 is in the relaxed position and the second surgical tool 306b is depicted as extended through the cannula 104 and out the distal end 106b. The second surgical tool 306b also extends through the radial biasing device 602 and, more particularly, through the compliant stabilizing member 606, which exhibits a relaxed inner diameter 608. In some embodiments, the relaxed inner diameter 608 is equal to or lightly larger than the outer diameter 310 of the second surgical tool 306b. In other embodiments, however, the relaxed inner diameter 608 may be smaller than the outer diameter 310 and configured to conform (expand) to the outer surface of the second surgical tool 306b, without departing from the scope of the disclosure. The compliant stabilizing member 606 operates to center the second surgical tool 306b within the lumen 302 and eliminate or significantly minimize unintended oscillation movement and/or vibration of the second surgical tool 306b.

FIG. 6C shows the radial biasing device 602 in the extended position. The radial biasing device 602 is able to transition to the extended position when a surgical tool having a diameter larger than the relaxed inner diameter 608 (FIG. 6B) of the compliant stabilizing member 606 is introduced into the cannula 104 and interacts with the radial biasing device 602. In the illustrated embodiment, the first surgical tool 306a is extended through the cannula 104 and the larger outer diameter 308 forces the compliant stabilizing member 606 to radially expand to an extended diameter 610 that accommodates the larger-diameter first surgical tool 306a. Since the compliant stabilizing member 606 is made of an elastic material, the compliant stabilizing member 606 may be able to radially expand as needed. In the illustrated embodiment, the extended diameter 610 is approximately the same size as the outer diameter 308 of the first surgical tool 306a. Accordingly, the compliant stabilizing member 606 may be configured to compliantly expand and the extended diameter 610 will conform to the outer diameter of the surgical tool passing therethrough.

In one or more embodiments, the compliant stabilizing member 606 may be made of or otherwise coated with any of the lubricious (e.g., slippery or slick) materials mentioned herein, thereby reducing the drag force of any surgical tool passing therethrough.

Figure 7A:
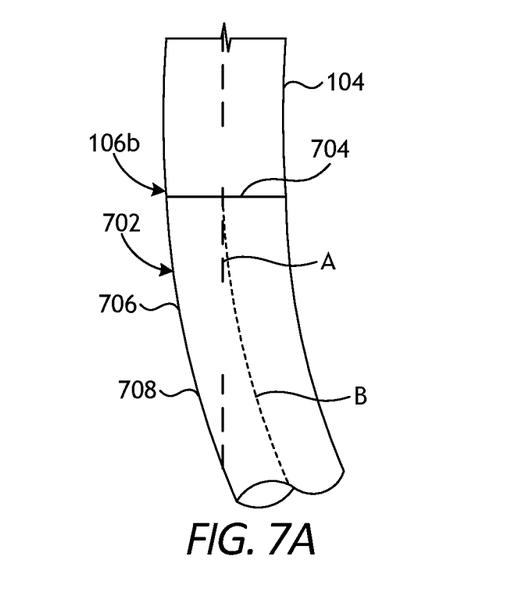
FIG. 7A is a side view of another example radial biasing device that may be used with the trocar assembly of FIGS. 1-3.

FIG. 7A is a side view of another example radial biasing device 702 that may be used with the trocar assembly 100 of FIGS. 1-3, according to one or more embodiments of the present disclosure. Similar to the radial biasing device 402 of FIGS. 4A-4B, the radial biasing device 702 may be coupled to or otherwise arranged at or near the distal end 106b of the cannula 104 at an interface 704 between the annular body 406 and the cannula 104. The radial biasing device 702 may include an annular body 706 that also constitutes a compliant stabilizing member 708. In the illustrated embodiment, the annular body 706 and compliant stabilizing member 708 are in the form of a tube or hose that extends distally from the distal end 106b of the cannula 104. Moreover, the annular body 706 and compliant stabilizing member 708 may be bent or curved such that a centerline B of the radial biasing device 702 diverges from the centerline A of the cannula 104 as the annular body 706 extends distally from the distal end 106b of the cannula 104.

The interface 704 may be similar to the interface 404 of FIGS. 4A-4B and 5A-5C. In the illustrated embodiment, for example, the interface 704 comprises a type of butt joint where the radial biasing device 702 is coupled directly to the distal end 106b of the cannula 104. In such embodiments, the radial biasing device 702 may be coupled to the cannula 104 with one or more mechanical fasteners, welding, ultrasonic welding, brazing, an adhesive, or any combination thereof. In other embodiments, however, the interface 704 may comprise a threaded engagement between the biasing device 702 and the distal end 106b of the cannula 104, similar to the engagement shown in FIG. 5A. In yet other embodiments, the radial biasing device 702 may be secured within the distal end 106b of the cannula 104 via an interference or shrink fit, or a mechanical attachment (e.g., a bayonet connection), similar to the engagements shown in FIGS. 5B and 5C, respectively. In even further embodiments, the radial biasing device 702 may extend about the exterior of the distal end 106b of the cannula 104, similar to the radial biasing device 602 of FIGS. 6A-6C, without departing from the scope of the disclosure.

Figure 7B:
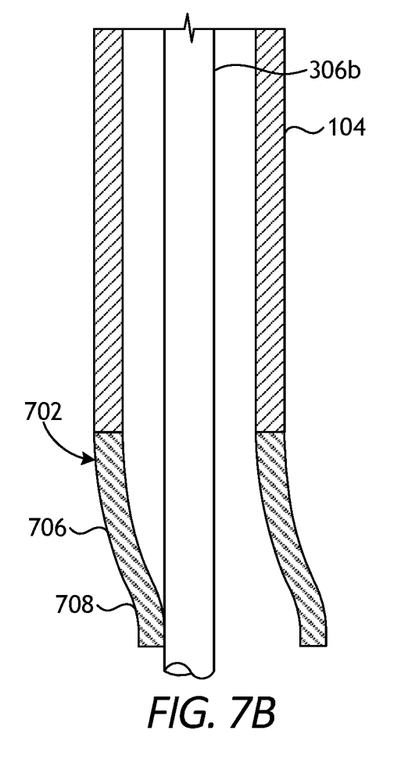
FIGS. 7B and 7C are cross-sectional side views of the radial biasing device of FIG. 7A depicting example operation.
Figure 7C:
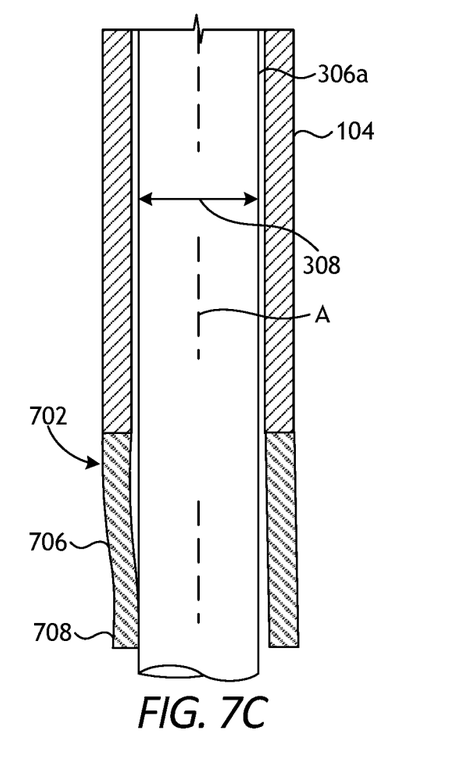

FIGS. 7B and 7C are cross-sectional side views of the radial biasing device 702 depicting example operation, according to one or more embodiments. All or a portion of the radial biasing device 702 may be made of a pliable or elastic material to enable the radial biasing device 702 to transition between a generally relaxed position, as shown in FIG. 7B, and an extended position, as shown in FIG. 7C. Suitable elastic materials include those mentioned herein with respect to the radial biasing device 402 of FIGS. 4A-4B.

In FIG. 7B, the radial biasing device 702 is generally in the relaxed position and the second surgical tool 306b is depicted as extended through the cannula 104 and out the distal end 106b. The second surgical tool 306b also extends through the radial biasing device 702. A portion of the annular body 706 and compliant stabilizing member 708 may engage the outer surface of the second surgical tool 306b to provide hysteretic damping. Moreover, engaging the outer surface of the second surgical tool 306b provides at least two points of contact for the second surgical tool 306b as it extends through the surgical tool 100 (FIGS. 1-3); i.e., a first point of contact at the first and/or second seal assemblies 204a, b (FIGS. 2 and 3) and a second point of contact against the inner wall of the annular body 706 and compliant stabilizing member 708. These two (or more) points of contact help eliminate or significantly minimize unintended oscillation movement and/or vibration of the second surgical tool 306b.

FIG. 7C shows the radial biasing device 702 in the extended position. The radial biasing device 702 transitions to the extended position when a surgical tool having a larger diameter is introduced into the cannula 104 and interacts with the radial biasing device 702. In the illustrated embodiment, the first surgical tool 306a is extended through the cannula 104 and the larger outer diameter 308 engages the annular body 706 and compliant stabilizing member 708 and forces the annular body 706 to straighten toward the centerline A. Since the radial biasing device 702 is made of an elastic material, the annular body 706 and compliant stabilizing member 708 are able to compliantly bend with the first surgical tool 306a and toward the centerline A. The annular body 706 and compliant stabilizing member 708 also engage the outer surface of the first surgical tool 306a, which provides at least two points of stabilizing contact as it extends through the surgical tool 100 (FIGS. 1-3), as discussed above.

In one or more embodiments, the annular body 706 and compliant stabilizing member 708 may be made of or otherwise coated with any of the lubricious (e.g., slippery or slick) materials mentioned herein, thereby reducing the drag force of any surgical tool passing therethrough.

While the radial biasing device 702 is shown in FIGS. 7A-7C as being coupled to or arranged at or near the distal end 106b of the cannula 104, the radial biasing device may alternatively comprise or make up the entire length of the cannula 104, without departing from the scope of the disclosure.

The radial biasing devices 402, 602, and 702 shown and described in the foregoing figures are only examples of providing an elastic biasing means used to center (or stabilize) surgical tools within the cannula 104. Those skilled in the art will readily appreciate that there are several other ways and means to provide radial biasing devices with elastic biasing means or functions. In some embodiments, for example, an extension spring may be embedded within a reasonably compliant material and formed into an annular structure positioned within the lumen 302. The combination of the extension spring and the compliant material may provide the elastic biasing means necessary to center surgical tools within the cannula 104. In other embodiments, a pleated member may be positioned within (or external to) the cannula 104, and the pleats of the pleated member may provide the elastic biasing means necessary to center surgical tools within the cannula 104. In yet other embodiments, a helical flat spring may be positioned within the cannula 104 and used to expand radially inward and outward to provide the elastic biasing means necessary to center surgical tools within the cannula 104.

Embodiments Disclosed Herein Include:

A. A trocar assembly that includes a trocar housing that defines a working chamber, a cannula having a proximal end and a distal end and defining a lumen that extends between the proximal and distal ends, wherein the cannula is coupled to the trocar housing at the proximal end to facilitate communication between the lumen and the working chamber, and a radial biasing device arranged at or near the distal end of the cannula and including an annular body coupled to the cannula and a compliant stabilizing member transitionable between a relaxed position and an extended position when acted upon by a surgical tool introduced into the lumen and passing through the compliant stabilizing member.

B. A method of using a trocar assembly that includes introducing a surgical tool into a working chamber defined by a trocar housing, wherein the working chamber communicates with a lumen defined by a cannula coupled to the trocar housing, extending the surgical tool into the lumen, and engaging an outer surface of the surgical tool on a radial biasing device arranged at or near the distal end of the cannula and thereby centering the surgical tool within the lumen minimizing oscillation movement and/or vibration of the surgical tool, wherein the radial biasing device includes an annular body coupled to the cannula and a compliant stabilizing member.

C. A radial biasing device that includes an annular body configured to be coupled to a distal end of a cannula of a trocar assembly, and a compliant stabilizing member made of an elastic material and transitionable between a relaxed position and an extended position when acted upon by a surgical tool passing through the compliant stabilizing member, wherein the compliant stabilizing member has a relaxed inner diameter in the relaxed position and an extended inner diameter greater than the inner diameter in the extended position.

Each of embodiments A, B, and C may have one or more of the following additional elements in any combination: Element 1: wherein the annular body is coupled to the cannula via an attachment means selected from the group consisting of one or more mechanical fasteners, a threaded engagement, welding, ultrasonic welding, brazing, an adhesive, an interference fit, a shrink fit, a mechanical attachment, and any combination thereof. Element 2: wherein the compliant stabilizing member is made of an elastic material selected from the group consisting of rubber, silicone, ethylene vinyl acetate, nylon, vinyl, spandex, polyurethane, polyethylene, polypropylene, and any combination thereof. Element 3: wherein the compliant stabilizing member is coated with a lubricious material. Element 4: wherein the compliant stabilizing member exhibits a relaxed inner diameter in the relaxed position and exhibits an extended inner diameter in the extended position, and wherein the extended inner diameter is greater than the relaxed inner diameter. Element 5: wherein the compliant stabilizing member transitions between the relaxed and extended positions based on an outer diameter of the surgical tool introduced into the lumen and passing through the compliant stabilizing member. Element 6: wherein the compliant stabilizing member comprises a ring arranged within the annular body and is coupled to the annular body with an annular flange extending between the compliant stabilizing member and the annular body. Element 7: wherein the compliant stabilizing member is forced out of the annular body when the surgical tool introduced into the lumen and passing through the compliant stabilizing member has an outer diameter larger than a relaxed inner diameter of the compliant stabilizing member. Element 8: wherein the annular body is coupled to an exterior of the cannula and the compliant stabilizing member extends distally from the annular body and tapers inward. Element 9: wherein the annular body and the compliant stabilizing member are separate component parts coupled together. Element 10: wherein the annular body and the compliant stabilizing member jointly comprise a curved tube having a centerline that diverges from a centerline of the cannula as the annular body and the compliant stabilizing member extend distally from the distal end of the cannula.

Element 11: wherein the compliant stabilizing member is made of an elastic material selected from the group consisting of rubber, silicone, ethylene vinyl acetate, nylon, vinyl, spandex, polyurethane, polyethylene, polypropylene, and any combination thereof. Element 12: further comprising mitigating drag against the outer surface of the surgical tool with a lubricious material coated on the compliant stabilizing member. Element 13: wherein the compliant stabilizing member exhibits a relaxed inner diameter in a relaxed position and exhibits an extended inner diameter in an extended position, and wherein the extended inner diameter is greater than the relaxed inner diameter, the method further comprising transitioning the compliant stabilizing member to the extended position based on an outer diameter of the surgical tool. Element 14: wherein the compliant stabilizing member comprises a ring arranged within the annular body and is coupled to the annular body with an annular flange, the method further comprising forcing the compliant stabilizing member out of the annular body when the surgical tool passes through the compliant stabilizing member and has an outer diameter larger than a relaxed inner diameter of the compliant stabilizing member. Element 15: wherein the annular body is coupled to an exterior of the cannula and the compliant stabilizing member extends distally from the annular body and tapers inward, and wherein engaging the outer surface of the surgical tool on the radial biasing device comprises radially expanding the compliant stabilizing member from a relaxed inner diameter to an extended inner diameter.

Element 16: wherein the compliant stabilizing member comprises a ring arranged within the annular body and is coupled to the annular body with an annular flange extending between the compliant stabilizing member and the annular body. Element 17: wherein the annular body is coupled to an exterior of the cannula and the compliant stabilizing member extends distally from the annular body and tapers inward.

By way of non-limiting example, exemplary combinations applicable to A, B, and C include: Element 4 with Element 5; Element 6 with Element 7; and Element 8 with Element 9.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

The terms "proximal" and "distal" are defined herein relative to a surgeon or robotic surgical system having an interface configured to mechanically and electrically couple a surgical tool to a robotic manipulator. The term "proximal" refers to the position of an element closer to the surgeon or the robotic manipulator and the term "distal" refers to the position of an element further away from the surgeon or the robotic manipulator. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A trocar assembly, comprising:
   a trocar housing that defines a working chamber;
   a cannula having a proximal end and a distal end and defining a lumen that extends between the proximal and distal ends, wherein the cannula is coupled to the trocar housing at the proximal end to facilitate communication between the lumen and the working chamber; and
   a radial biasing device arranged at or near the distal end of the cannula and including an annular body coupled to the cannula and a compliant stabilizing member transitionable between a relaxed position and an extended position when acted upon by a surgical tool introduced into the lumen and passing through the compliant stabilizing member,
   wherein the compliant stabilizing member is open in the relaxed position to receive the surgical tool, and
   wherein the compliant stabilizing member comprises a ring arranged within the annular body and coupled to the annular body with an annular flange extending between the compliant stabilizing member and the annular body.

2. The trocar assembly of claim 1, wherein the annular body is coupled to the cannula via an attachment means selected from the group consisting of one or more mechanical fasteners, a threaded engagement, welding, ultrasonic welding, brazing, an adhesive, an interference fit, a shrink fit, a mechanical attachment, and any combination thereof.

3. The trocar assembly of claim 1, wherein the compliant stabilizing member is made of an elastic material selected from the group consisting of rubber, silicone, ethylene vinyl acetate, nylon, vinyl, spandex, polyurethane, polyethylene, polypropylene, and any combination thereof.

4. The trocar assembly of claim 1, wherein the compliant stabilizing member is coated with a lubricious material.

5. The trocar assembly of claim 1, wherein the compliant stabilizing member exhibits a relaxed inner diameter in the relaxed position and exhibits an extended inner diameter in the extended position, and wherein the extended inner diameter is greater than the relaxed inner diameter.

6. The trocar assembly of claim 5, wherein the compliant stabilizing member transitions between the relaxed and extended positions based on an outer diameter of the surgical tool introduced into the lumen and passing through the compliant stabilizing member.

7. The trocar assembly of claim 1, wherein the compliant stabilizing member is forced out of the annular body when the surgical tool introduced into the lumen and passing through the compliant stabilizing member has an outer diameter larger than a relaxed inner diameter of the compliant stabilizing member.

8. A method of using a trocar assembly, comprising:
introducing a surgical tool into a working chamber defined by a trocar housing, the working chamber communicating with a lumen defined by a cannula coupled to the trocar housing;
extending the surgical tool into the lumen;
engaging an outer surface of the surgical tool on a radial biasing device arranged at or near a distal end of the cannula and thereby centering the surgical tool within the lumen and minimizing oscillation movement and/or vibration of the surgical tool, wherein the radial biasing device includes an annular body coupled to the cannula and a compliant stabilizing member, the compliant stabilizing member exhibiting a relaxed inner diameter in a relaxed position and an extended inner diameter in an extended position and greater than the relaxed inner diameter, and wherein the compliant stabilizing member is open to receive the surgical tool; and
forcing the compliant stabilizing member out of the annular body when the surgical tool passes through the compliant stabilizing member and has an outer diameter larger than the relaxed inner diameter of the compliant stabilizing member.

9. The method of claim 8, wherein the compliant stabilizing member is made of an elastic material selected from the group consisting of rubber, silicone, ethylene vinyl acetate, nylon, vinyl, spandex, polyurethane, polyethylene, polypropylene, and any combination thereof.

10. The method of claim 8, further comprising mitigating drag against the outer surface of the surgical tool with a lubricious material coated on the compliant stabilizing member.

11. The method of claim 8, wherein, the method further comprising transitioning the compliant stabilizing member to the extended position based on an outer diameter of the surgical tool.

12. A radial biasing device, comprising:
an annular body configured to be coupled to a distal end of a cannula of a trocar assembly; and
a compliant stabilizing member made of an elastic material and transitionable between a relaxed position and an extended position when acted upon by a surgical tool passing through the compliant stabilizing member, the compliant stabilizing member comprising a ring arranged within the annular body and being coupled to the annular body with an annular flange extending between the compliant stabilizing member and the annular body,
wherein the compliant stabilizing member has a relaxed inner diameter in the relaxed position and an extended inner diameter greater than the relaxed inner diameter when in the extended position, and
wherein the compliant stabilizing member is open in the relaxed position to receive the surgical tool.

13. A trocar assembly, comprising:
a trocar housing that defines a working chamber;
a cannula having a proximal end and a distal end and defining a lumen that extends between the proximal and distal ends, wherein the cannula is coupled to the trocar housing at the proximal end to facilitate communication between the lumen and the working chamber; and
a radial biasing device arranged at or near the distal end of the cannula and including an annular body coupled to the cannula and a compliant stabilizing member transitionable between a relaxed position and an extended position when acted upon by a surgical tool introduced into the lumen and passing through the compliant stabilizing member,
wherein the compliant stabilizing member is open in the relaxed position to receive the surgical tool, and
wherein the annular body is coupled to an exterior of the cannula and the compliant stabilizing member extends distally from the annular body and tapers inward.

14. The trocar assembly of claim 13, wherein the annular body and the compliant stabilizing member are separate component parts coupled together.

15. The trocar assembly of claim 13, wherein the annular body is coupled to the cannula via an attachment means selected from the group consisting of one or more mechanical fasteners, a threaded engagement, welding, ultrasonic welding, brazing, an adhesive, an interference fit, a shrink fit, a mechanical attachment, and any combination thereof.

16. A trocar assembly, comprising:
a trocar housing that defines a working chamber;
a cannula having a proximal end and a distal end and defining a lumen that extends between the proximal and distal ends, wherein the cannula is coupled to the trocar housing at the proximal end to facilitate communication between the lumen and the working chamber; and
a radial biasing device arranged at or near the distal end of the cannula and including an annular body coupled to the cannula and a compliant stabilizing member transitionable between a relaxed position and an extended position when acted upon by a surgical tool introduced into the lumen and passing through the compliant stabilizing member,
wherein the compliant stabilizing member is open in the relaxed position to receive the surgical tool, and
wherein the annular body and the compliant stabilizing member jointly comprise a curved tube having a centerline that diverges from a centerline of the cannula as the annular body and the compliant stabilizing member extend distally from the distal end of the cannula.

17. The trocar assembly of claim 16, wherein the annular body is coupled to the cannula via an attachment means selected from the group consisting of one or more mechanical fasteners, a threaded engagement, welding, ultrasonic welding, brazing, an adhesive, an interference fit, a shrink fit, a mechanical attachment, and any combination thereof.

18. A method of using a trocar assembly, comprising:
introducing a surgical tool into a working chamber defined by a trocar housing, the working chamber communicating with a lumen defined by a cannula coupled to the trocar housing;
extending the surgical tool into the lumen;
engaging an outer surface of the surgical tool on a radial biasing device arranged at or near a distal end of the cannula and thereby centering the surgical tool within the lumen and minimizing oscillation movement and/or vibration of the surgical tool,
wherein the radial biasing device includes an annular body coupled to the cannula and a compliant stabilizing member open to receive the surgical tool, the annular body being coupled to an exterior of the cannula and the compliant stabilizing member extending distally from the annular body and tapering inward, and wherein engaging the outer surface of the surgical tool on the radial biasing device comprises radially expanding the compliant stabilizing member from a relaxed inner diameter to an extended inner diameter.

19. The method of claim 18, further comprising mitigating drag against the outer surface of the surgical tool with a lubricious material coated on the compliant stabilizing member.

20. A radial biasing device, comprising:
an annular body coupled to an exterior of a distal end of a cannula of a trocar assembly; and
a compliant stabilizing member extending distally from the annular body and tapering inward, the compliant stabilizing member being made of an elastic material and transitionable between a relaxed position and an extended position when acted upon by a surgical tool passing through the compliant stabilizing member,
wherein the compliant stabilizing member has a relaxed inner diameter in the relaxed position and an extended inner diameter greater than the relaxed inner diameter when in the extended position, and
wherein the compliant stabilizing member is open in the relaxed position to receive the surgical tool.

* * * * *